Figure 1:
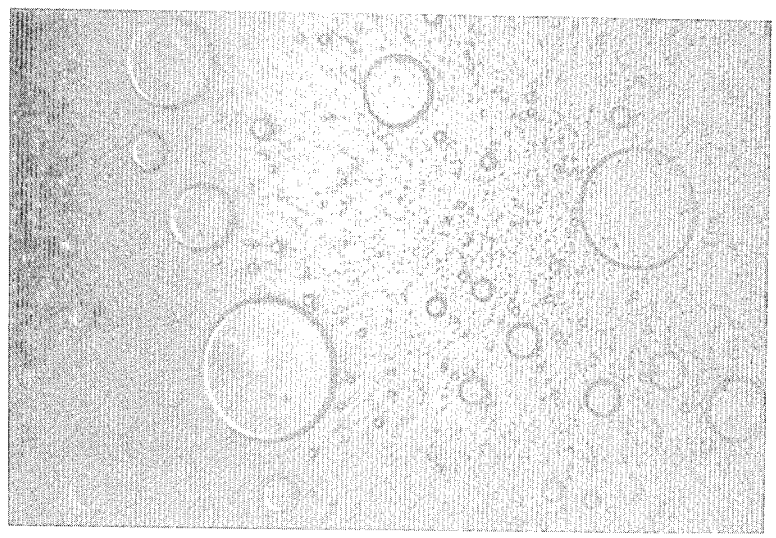

United States Patent [19]

Holzner

[11] Patent Number: 4,803,195

[45] Date of Patent: Feb. 7, 1989

[54] PERFUME COMPOSITION WITH DEODORISING OR ANTIPERSPIRANT ACTION

[75] Inventor: Günter Holzner, Grand-Lancy, Switzerland

[73] Assignee: Firmenich S.A., Geneva, Switzerland

[21] Appl. No.: 157,422

[22] Filed: Feb. 17, 1988

[30] Foreign Application Priority Data

Feb. 20, 1987 [CH] Switzerland ............................ 647/87

[51] Int. Cl.$^4$ .................................................. A61K 7/46
[52] U.S. Cl. ............................................ 512/4; 512/1
[58] Field of Search ........................................ 512/1, 4

[56] References Cited

U.S. PATENT DOCUMENTS

| | | | |
|---|---|---|---|
| 4,011,311 | 3/1977 | Noomen | 512/1 |
| 4,067,824 | 1/1978 | Teng et al. | 512/4 |
| 4,089,814 | 5/1978 | Schmolka | 512/1 |
| 4,226,889 | 10/1980 | Yuhas | 512/4 |
| 4,668,430 | 5/1987 | Schmolka | 512/1 |

Primary Examiner—Werren B. Lone
Attorney, Agent, or Firm—Pennie & Edmonds

[57] ABSTRACT

Personal care composition having deodorant or antiperspirant activity and containing, in addition to an active deodorant or antiperspirant base, a perfuming base, either in the form of an aqueous emulsion, or in micro-encapsulated form. The perfume base is combined with a film-forming substrate and an emulsifying agent.

The said composition has the advantage of releasing the volatile constituents of the perfume at the appropriate moment by the action of a source of moisture, in particular sweat. It also has the advantage that it gives rise to a re-encapsulation in situ, for example on the skin itself, of active constituents in the drying phase. It is suitable in particular for the manufacture of articles for personal care, such as deodorants and antiperspirants in the form of sticks, roll-on devices, smooth-ons or aerosols and pressure vaporizers.

6 Claims, 3 Drawing Sheets

PERFUME COMPOSITION WITH DEODORISING OR ANTIPERSPIRANT ACTION

BRIEF SUMMARY OF THE INVENTION

This invention relates to a perfuming composition with deodorant or antiperspirant action for use in personal care, characterized in that it contains, in addition to an active deodorant or antiperspirant base, a perfuming base, either in the form of an aqueous emulsion, or in microencapsulated form, the said perfuming base being combined with a. a solid film-forming substrate chosen from polyvinyl acetate, polyvinyl alcohol, dextrins, natural or modified starch, vegetable gums, pectins, xanthans, carboxymethylcellulose, methylcellulose, hydroxymethylcellulose and lipoheteropolysaccharides, and b. an emulsifying agent chosen from mono- or diglycerides of fatty acids, esters derived from the combination of fatty acids with sorbitol or a saccharide, or their alkoxylated derivatives, or an ester of tartaric, citric, ascorbic or lactic acid.

The invention relates further to a deodorant or antiperspirant device or article for use in personal care, characterized in that it contains the perfuming composition defined above.

BACKGROUND OF THE INVENTION

The perfuming of personal care products, such as deodorants or antiperspirants, plays a major, and often determining, role for the consumer. Although different in their mode of action and in their formulation, these two groups of products are often treated under the same heading.

If, on the one hand, the function of a deodorant is to mask body odour arising in the armpit, for example, by means of a perfume and to inhibit the growth of the bacteria which are responsible for creating the unpleasant odours generally associated with sweat, products sold as deodorants are often based solely on an alcohol solution of perfume and a bactericide. Generally, this is a mild medium in which the components of the perfume are unlikely to break down. It is different for an antiperspirant, in which the active ingredients, generally aluminium salts, attack the perfume, which makes the latter particularly unstable. This phenomenon gives rise to changes in the scent and often to the appearance of discolouration.

The perfumer has to accommodate himself to this state of facts and to limit accordingly the choice of raw materials which may be used in such systems.

Current commercial products may furhter be distinguished from one another by their form of presentation, whether solutions, a cream, a stick, or a powder. These products are distinguised, then, by their mode of application. In this way, one can distinguish between aerosols, sticks, roll-ons, or smooth-ons. Each of these devices has individual technical characteristics, and the perfuming of their active ingredient requires a solution adapted to these distinct features [see, for example, in this connexion: The Reheis (registered trade mark) Report, vol. III (1985) and Herbert P. Fiedler, Der Schweiss, Editio Cantor KG, Aulendorf i. Wurtt., (1968)].

In order to suppress the inherent disadvantages of the reactivity of the medium towards the perfuming agent, particularly in very acidic conditions, the cosmetics industry has endeavoured to develop active antiperspirant bases of a varied nature, based in the majority of cases, however, on aluminium salts [see, for example, U.S. Pat. No. 3,030,274; NL No. patent 93662; U.S. Pat. No. 3,018,223; FR Pat. No. 1,486,857]. To this end, it is appropriate to mention the growing success of antiperspirant bases on the use of CHLORHYDROL (trade mark registered by Reheis Chemical Co., Division of Armour Pharmaceutical Co.) or of LOCRON (trade mark registered by Hoechst AG), aluminium chlorohydrates having moderately acidic properties.

Practice has shown that when a currently available device is used, the diffusion of the perfume on the skin is at its maximum at the time of application. It fades progressively during the ensuing period, the length of which is generally related to the capacity of the product to remain on the skin of the user. However, this period is barely more than a few hours even in the best of cases.

In order to ensure greater stability of the perfumes, the industry has resorted to the technique of microencapsulation. In a microencapsulated system, the active perfuming ingredients are protected from the influence of aluminium salts or heavy metals, such as iron or lead, which are present in the base. However, such systems do not solve the problem of controlling the diffusion of the perfume. On contact with the skin and by the action of the sweat, the microcapsules enclosing the perfume dissolve, releasing their active perfuming ingredients, which diffuse in the surrounding atmosphere. The use is thus most aware of the perfume during the initial period of perspiration, but the perfume diffuses less and less thereafter. On dissolving, the microcapsules moreover cease to carry out their protective action, and the perfume is therefore exposed to the action of the acidic antiperspirant base.

The British patent No. 1,275,969 published on June 1, 1972 describes a deodorant composition in the form of an aerosol formed by deodorant capsules in a propellant mixture. The capsules are characterized in that they have walls which are soluble in water but insoluble in the propellant mixture and impermeable to the latter. A composition of this kind has the property of maintaining, at least in part, the active deodorant components in a stable medium until the same ingredients are released by the action of perspiration. This is to some extent a mixture which responds to the activation exerted by the user himself or herself. Experience has proven that a system of this kind could offer use which is satisfactory but limited, however, to a single activation. Once dissolved, the capsules could release the active deodorising ingredients and their action could last until they had completely evaporated.

We have discovered that, by a particular choice of ingredients used in the deodorant composition, it was possible to cause a reversible phenomenon of "reencapsulation" of the active deodorant ingredients, such that a plurality of successive activations could take place on the skin itself without the need to reapply the deodorant. A genuine re-encapsulation therefore takes place in situ during the drying phase of the skin following the perspiration period.

THE INVENTION

The object of the present invention is therefore a perfumed composition with deodorant and antiperspirant action intended for personal care, the composition having the advantage of permitting control of the activation and diffusion of the perfume over a period of time. A composition of this kind combines the need for protecting the active ingredients of the perfume and the wish to prolong the period of diffusion of the latter. This double action is a result of the phenomenon described above. When applied to the skin, the composition is first held at the surface of the emulsion by adhesion when the perfuming base is used in the form of an aqueous emulsion, by virtue of the binding effect of the substrate. Due to subsequent drying, which is assisted by the body head, the active air of the skin thus treated and which is assisted by the body head, the active perfuming base is held in the form of microscopic droplets covered with a protective water-soluble layer formed by the substrate, which will from now on be dry.

In this case, a simple system is involved which does not require the application of special devices for its use. Any conventional system of use current in cosmetics and currently used for the application of deodorants and antiperspirants can be used. In this connexion, creams, roll-ons, smooth-ons or powders can be mentioned.

The same applies when the active perfuming base is used in a microencapsulated form, generally in suspension in an alcohol solution. The perfuming base, combined in advance with a solid film-forming substrate and an emulsifying agent, is atomised according to conventional techniques in a spraydrying tower. The microcapsules obtained, enclosing the perfuming base, are mixed with a deodorant or antiperspirant base and then suspended in a base substantially composed of waxes according to the technique used to manufacture sticks, or in a propellant mixture for the manufacture of aerosols.

The following may be used as a solid film-forming substrate: polyvinyl acetate, polyvinyl alcohol, dextrins (natural or modified), starch (natural or modified), vegetable gums, alginates, carrageenans, pectins, xanthans, or derivatives of cellulose such as, for example, carboxymethylcellulose, methylcellulose and hydroxymethylcellulose. These are compounds which may be defined by the generic term "gums" (cf. in this connexion, the definition given in Kirk-Othmer, Encyclopedia of Chemical Technology, 2nd edition, vol. 10, p.741).

This term "natural gums", such as gum arabic for example, covers seaweed extracts, such as agar, carregeenans, furcellarane and modified or semi-synthetic gums. These are cellulose and starch derivatives and gums formed by microbe fermentation, such as heteropolysaccharides, for example biopolymers known as emulsans (cf. European Patent Application No. 178 443 published on 23.04.86).

As an emulsifying agent, mono- or diglycerides of fatty acids, esters derived from the combination of fatty acids with sorbitol or a monosaccharide, or their alkoxylated derivatives, or an ester of tartaric, citric, ascorbic or lactic acid may be used.

The composition according to the invention also contains a perfuming base. In the terms of the present invention, "perfuming base" is to be understood as any perfuming substance or mixture of perfuming substances, whether in isolation or in a solution or suspension in their natural dilutants, solvents or co-ingredients. This term includes, in particular, organic solutions which are not generally miscible in water and which have a high vapour tension. Such perfuming bases can be formed by compounds belonging to distinct chemical classes and including, for example, esters, ethers, alcohols, aldehydes, ketones, acetals, nitriles, terpenic hydrocarbons, nitrogen- or sulphur-containing heterocyclic compounds and essential oils of natural origin. The particular choice of the perfuming base depends on the perfuming effect required, the nature of the product to be perfumed, and of course, on the taste and preference of the perfumer in question.

Typical examples of usable perfuming compounds are given in literature and, in this connexion, S. Arctander, Perfume and Flavor Chemicals, Montclair, N.J. (USA)(1969) may be cited.

The composition according to the invention may also contain bactericidal agents with a disinfectant or germicidal action, as well as bacteriostatic agents.

Although it is difficult to define a precise range of concentration of its constituents, the perfuming composition according to the invention preferably contains (by weight):
2 to 20% of solid film-forming substate,
0.1 to 10% of emulsifying agent,
0.1 to 5% of perfuming base,
5 to 25% of active deodorant or antiperspirant base, the remainder consisting of water, inert solvents and/or excipients, and optionally containing disinfecting, germicidal or bacteriostatic agents.

A deodorant base is to be understood as being a substance capable of masking body odour and inhiniting the growth of the bacteria responsible for decomposing sweat. A considerable number of bactericidal and bacteriostatic products are known and used to this end. By way of example, the following may be used: hexachlorophene, dichlorophenol, trichlorosalicylanilide (Anobial), tribromosalicylanilide (TBS), tetrachlorosalicylanilide (TCSA) and trichlorocarbanilide (TCC).

As an antiperspirant base, aluminum salts, for example the abovementioned aluminium chlorhydrate, are preferably used. Different compositions are proposed on the market as products with an antiperspirant base: CHLORHYDROL, CHORACEL and REZAL (trade marks registered by Reheis Chem. Co., USA) are examples. These are complex aluminium or aluminium and zirconium salts. Other antiperspirant bases are described in specialist literature (cf. for example, Herbert P. Fiedler, Der Schweiss, Edition Cantor KG, Aulendorf i. Wurtt., FRG).

The perfuming composition according to the invention is particularly suitable for the manufacture of articles intended for personal care. These may occur in many different forms. As mentioned above, these may be sticks, roll-ons, smooth-ons, or aerosols or mechanically or manually pressurised vaporisers.

The composition according to the invention is obtained by mixing its ingredients by means of conventional apparatus. The technique of mixing is known per se and any detailed explanation is superfluous here. The method depends essentially on the final article to be manufactured. Thus, for example, if an antiperspirant composition is to be manufactured intended for use by means of a ball device of the roll-on type, the process is as follows.

At room temperature, the powder formed by the solid film-forming substrate, for example a mixture of maltodextrins, is poured into the required amount of demineralised water. When the powder is completely dissolved, the antiperpirant base is added to the solution obtained and the mixture is brewed and heated to 70° C., then, at the same temperature, the emulsifying agent is added using a homogenising mixer. After several minutes of brewing, the mixture is cooled to room temperature and the perfuming base is added at about 40° C. The perfumed viscous mass is finally poured into ball-top roll-on-type containers.

If a wet antiperspirant composition is to be manufactured intended for use by means of a mechanically or manually pressurised vaporising device, the following process is preferably used.

The solid substrate in powdered form is poured at room temperature into water and brewed for about 1 hour until completely dissolved. The active antiperspirant base (aluminium chlorohydrate, for example) in ethanol is added to the resulting solution, followed by the perfuming base mixed in advance with an emulsifier. The mixture is then poured into vaporising containers.

The invention is illustrated non-limitatively by the following examples, in which the tempratures are indicated in centigrade and the abbreviations have the meanings commonly used in the art.

EXAMPLE 1

Antiperspirant composition for roll-on

An antiperspirant composition of the cream type to be incorporated in a ball-top dispenser of the roll-on type was prepared by adding by small portions a mixture consisting of 8.90 g of Glucidex 21 (maltodextrim DE 20-23)[1]
1.00 g of Nadex 722 (maltodextrin DE 9-12)[2]
0.10 g of sodium alginate
(1) Roquette Freres
(2) Grain Processing Corp.
to 65 g of demineralised water.

The mixture is brewed for 2 hours until the ingredients are completely dissolved, then 20 g of Locron (Locron L, aluminium chlorohydrate, 50% solution Heochst AG) was added. After bringing the temperature of the mixture to 70°, 4 g of Emulgade 1000 NI (self-emulsifying, non-ionogenic wax, Henkel AG) is added during vigourous stirring by means of an Ultra Turrax homogeniser. After several minutes of homogenisation, the mixture was cooled to room temperature and 1 g of perfume (Vera 72276/B, eau-do-Cologne-type, Firmenich SA, Geneva) was added at about 40°. The mixture obtained was finally poured into roll-on-type dispenser containers.

EXEMPLE 2

Antiperspirant composition for roll-on

An antiperspirant composition of the cream type to be incorporated in a ball-top roll-on-type dispenser was prepared by adding by small portions 10 g of Capsul (modified maize starch, National Starch) to 63.95 g of demineralised water. After 2 hours' brewing, a mixture was added consisting of:

0.10 g of Tween 20 (ethoxylated sorbitan monolaurate ICI, Atlas)
1.00 g of Triton CG 110 (alkyl glucoside, Rohm & Hass) and
0.05 g of Emulsan (Petroferm, bipolymer)
then 10 g of Locron L (Hoechst AG) was added and the mixture heated to 70° C. At this temperature, 4 g of Emulgade 1000 NI (Henkel AG) was added during vigorous stirring by means of homogenising apparatus. After a few minutes' brewing, the mixture was cooled to room temperature and 1 g perfume (Surf 635 040 E, of the aldehyde, flowery, green type, Firmenich SA, Geneva) was added. The mixture obtained was finally poured into roll-on-type dispenser containers.

EXAMPLE 3

Antiperspirant compositions for roll-on

Antiperspirant compositions having a clear appearance to be incorporated in ball-top roll-on-type dispenser containers were prepared as indicated in the preceding examples using the following ingredients (proportion by weight):

|  | a | b | c |
|---|---|---|---|
| I. Demineralised water | 39.0 | 51.6 | 56.6 |
| II. Natrosol 250 H[1] | 0.5 | 0.4 | 0.4 |
| Glucidex 21[2] | 10.0 | 7.2 | 4.0 |
| Glucidex 6[3] | — | — | 4.0 |
| Nadex[4] | — | 0.8 | — |
| III. Locron L[5] | 20.0 | 20.0 | 20.0 |
| 1,3-butylene glycol | 1.5 | 1.0 | 1.0 |
| Ethanol 95° | 26.0 | 16.0 | 10.0 |
| IV. Perfume[6] | 1.0 | 1.0 | 1.0 |
| Cremophor RH 40[7] | 2.0 | 2.0 | — |
| Lamacit 877[8] | — | — | 3.0 |
|  | 100.0 | 100.0 | 100.0 |

[1]hydroxyethylcellulose, Hercules Co.
[2]see example 1
[3]maltodextrin DE 5-8, Roquette Freres
[4]see example 1
[5]see example 1
[6]Gabriela 230.183, green, floral, fruity type, Firmenich SA, Geneva
[7]hydrogenated and ethoxylated castor oil, BASF AG
[8]ethoxylated nonylphenol, Chem. Verke, Grunau Part II was poured into water and brewed for 1 hour until the mixture was perfectly clear. Parts III and IV were then added successively to the solution obtained, with vigorous stirring, and the mixture was poured into roll-on containers.

EXAMPLE 4

Antiperspirant composition for smooth-on

An antiperspirant composition to be incorporated in a smooth-on-type container was prepared with the following ingredients:

| I. Demineralised water | 37.0 |
|---|---|
| II. Glucidex 21[1] | 9.0 |
| Nadex[2] | 1.0 |
| III. Locron L[3] | 40.0 |
| IV. Emulgade 1000 NI[4] | 8.0 |
| Arlacel 165[5] | 4.0 |
| V. Perfume[6] | 1.0 |
|  | 100.0 |

[1]see example 1
[2]-idem-
[3]-idem-
[4]-idem-
[5]glyceryl stearate + PEG 1000 stearate, ICI Altas
[6]Ambrosia UN 110.381/B, flowery, musky, woody type, Firmenich SA, Geneva Part II was dissolved in demineralised water and part III was added to the solution obtained, which was then heated to 70°. Part IV, which had been heated beforehand to 70°, was then added to the resulting mixture. After energetic brewing in an homogeniser, the mixture was cooled, and the perfume added during at approximately 40°.

EXAMPLE 5

Antiperspirant composition for pressurised spray

An antiperspirant composition to be used by means of a dispensing device comprising a spray system operated by mechanical or manual pressure ("Pump spray" or "squeeze bottle") was prepared with the following ingredients:

| | | |
|---|---|---|
| I. | Demineralised water | 39.0 |
| II. | Glucidex 21[1] | 10.0 |
| III. | Locron L[2] | 20.0 |
| | 1,3-butylene glycol | 1.5 |
| | Ethanol 95° | 26.5 |
| IV. | Perfume[3] | 1.0 |
| | Cremophor RH 40[4] | 2.0 |
| | | 100.0 |

[1] [2] see example 1
[3] Diabolo UN 110.382/B, flowery, green, hesperides type, Firmenich SA, Geneva
[4] see example 3

Part II was poured into demineralised water and brewed until a clear solution was obtained (1 hour). III and IV were then added successively during stirring and the resulting mixture was poured into spray containers.

EXAMPLE 6

Antiperspirant composition for aerosol spray

An antiperspirant composition to be applied by means of a "spray"-type dispenser was prepared by atomisation of the following mixture:

| | a |
|---|---|
| Water | 49.0 |
| Glucidex 21[1] | 36.0 |
| Nadex[2] | 4.0 |
| Sodium alginate | 0.8 |
| Capsul[3] | — |
| Tween 20 | 0.2 |
| Perfume[4] | 10.0 |
| | 100.0 |

[1] [2] see example 1
[3] modified maize starch, National Starch
[4] Surf 635.040 E, Firmenich SA, Geneva To carry out atomisation, a Leaflash-type apparatus (CCM Sulzer) is used:
Emulsion output: 50 kg/h,
Drying air: 320 m$^3$/h at 350° C. and 0.45 bar.
The base composition obtained was then used for the preparation of antiperspirant compositions for aerosol sprays by mixing with the following ingredients:

| | | |
|---|---|---|
| I. | Base composition (a) | 3.00 |
| | Aluminum chlorohydrate in micronised powder form (Hoechst) | 4.20 |
| | Aluminium chloride allantoinate (Merck) | 0.50 |
| | Isopropyl myristate | 6.85 |
| | Aerosil 200 (Degussa) | 0.25 |
| | Irgasan DP 300 (Ciba-Geigy) | 0.20 |
| | Propellant 11[1] | 50.00 |
| II. | Propellant 12[2] | 5.00 |
| | Propane/Butane[3] | 30.00 |
| | | 100.00 |

[1] monofluorotrichloromethane
[2] difluorodichloromethane
[3] 3.7 bar mixture

Part I was mixed in advance in order to obtain an homogeneous suspension, which was then poured into an aerosol container together with part II.

EXAMPLE 7

Antiperspirant composition for smooth-on

An antiperspirant composition for smooth-on was prepared with the following ingredients (proportion by weight):

| | | |
|---|---|---|
| I. | Cetyl alcohol | 9.0 |
| | Beeswax | 4.5 |
| | Stearic acid | 4.5 |
| | Finsolv TN[1] | 10.0 |
| | Arlacel 165[2] | 5.4 |
| II. | Aluminium chlorohydrate in micronised powder form[3] | 20.0 |
| | Talc | 5.0 |
| III. | Dow Corning fluid 345[4] | 35.6 |
| IV. | Base composition (a) or (b)[5] | 6.0 |
| | | 100.0 |

[1] benzoate of C12-C15 alcohol, Finetex
[2] see example 4
[3] see example 6
[4] volatile silicone oil
[5] see example 6

Part I was heated to 80° until all its ingredients had melted and parts II, III and IV were added to the molten mixture during thorough stirring. This was then left to cool to 40°-50° and poured into smooth-on-type containers.

EXAMPLE

Antiperspirant composition for sticks

An antiperspirant composition for dry sticks was prepared with the following ingredients (proportion by weight):

| | | |
|---|---|---|
| I. | Octadecanol | 19.0 |
| | Arlacel 165[1] | 1.0 |
| | PEG 1000[2] | 5.0 |
| II. | Aerosil 200[3] | 1.4 |
| | Talc | 1.0 |
| | Rezal 36 P[4] | 19.0 |
| III. | Dow Corning Fluid 345[5] | 47.6 |
| IV. | Base composition (a) or (b)[6] | 6.0 |
| | | 100.0 |

[1] see example 4
[2] polyglycol 1000, Hoechst
[3] Degussa
[4] complex zirconium chlorhydrate, Reheis Chem. Co.
[5] volatile silicone oil
[6] see example 6

Part I was heated to 90° until all the ingredients had dissolved completely, then heating was discontinued and II was added to the mixture obtained. Parts III and IV were then added successively during stirring. The mixture was finally poured into suitable moulds at approximately 65°.

EXAMPLE 9

Figure 2:
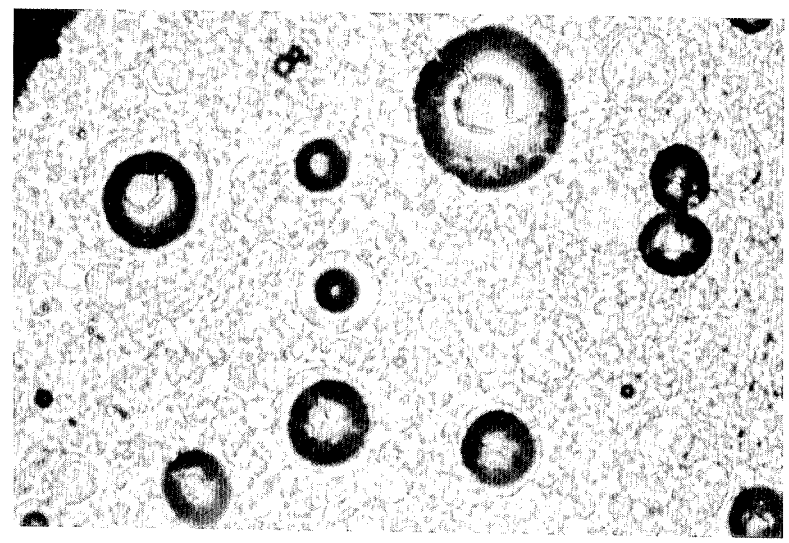

In order to show the reversible effect of the solubility and "reencapsulation" of the composition according to the invention, the antiperspirant composition obtained according to Example 3 was spread in a thin layer immediately after mixing on a slide and observed under a microscope (enlargement 600×). The reproduction of FIG. 1 shows the formation of distinct droplets of a variable diameter. After 20-30 minutes in air, the emulsion dried, forming a solid membrane surrounding a liquid phase (emulsion) formed by the perfume (FIG. 2).

Figure 3:
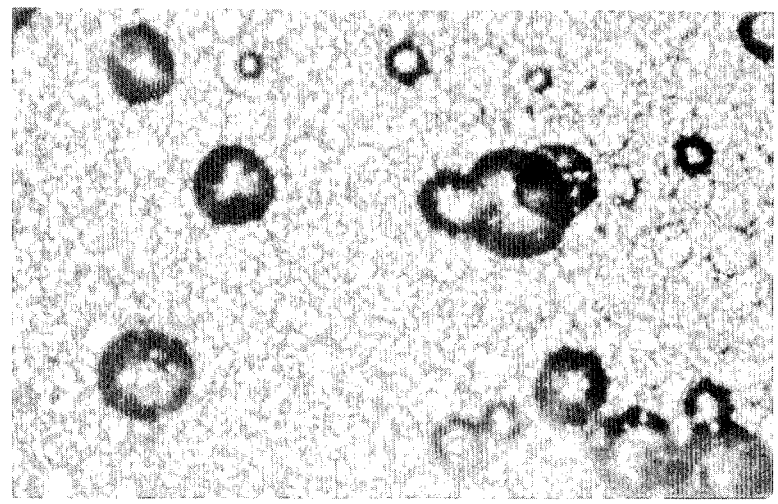

By moistening the capsules thus formed by the addition of a few drops of water, the solid membranes broke up, releasing the liquid perfume base, which, in direct contact with the air, partially evaporates into the surrounding atmosphere. On drying in the air once more, the microcapsules re-form, so that the remaining perfuming base is enclosed once more in the form of droplets by a solid protective membrane (FIG. 3).

This process may be repeated several times in the course of a day without any observable deterioration in the properties of the system until the perfume has completely evaporated.

A prolonged storage test showed that such a system retains its properties for at least one month.

The test carried out and described above shows one of the useful and unexpected properties of the composition according to the invention. The composition, which is used by spreading directly over the skin, at first dries to form the microcapsules enclosing the perfuming base. By the action of the sweat or on contact with a source of moisture, the perfuming base is released to be reencapsulated in situ when perspiration ceases. The release of the volatile constituents of the base, and consequently the masking and deodorant effect thereof, is genuinely effective at the appropriate moment; the user himself of herself thus controls this release physiologically.

EXAMPLE 10

An antiperspirant composition prepared according to Example 6 was applied by means of an aerosol spray in the axillary region of 10 male subjects aged between 21 and 36 years. The initial odour released by the skin thus treated was slight, and in certain cases nil. After about two hours, the subjects were involved in intense physical activity, such as represented by 20 minutes of basket-ball. An olfactory assessment carried out at this point showed that the release of perfume was intense. During the ensuing rest period (5 minutes), the drying of the sweat in the air resulted in a considerable decrease in the diffusion of the perfume. When the game resumed, perspiration caused a further release of perfume, which diminished or disappeared after a few minutes' drying in the air, as was noted by an assessment panel at the end of the game.

What I claim is:

1. A perfuming composition with deodorant or antiperspirant action for use in personal care, characterised in that it contains, in addition to an active deodorant or antiperspirant base, a perfuming base, either in the form of an aqueous emulsion, or in microencapsulated form, the said perfuming base being combined with
   a. a solid film-forming substrate chosen from polyvinyl acetate, polyvinyl alcohol, dextrins, natural or modified starch, vegetable gums, pectins, xanthans, carboxymethylcellulose, methylcellulose, hydroxymethylcellulose and lipoheteropholysaccharides, and
   b. an emulsifying agent chosen from mono- or diglycerides of fatty acids, esters derived from the combination of fatty acids with sorbitol or a saccharide, or their alkoxylated derivatives, or an ester of tartaric, citric, ascorbic or lactic acid.

2. A perfumed composition according to claim 1, characterised in that the aqueous emulsion consists of
   a. 2 to 20% of solid film-forming substrate
   b. 0.1 to 10% of emulsifying agent
   c. 0.1 to 5% of perfuming base
   d. 5 to 25% of active deodorant or antiperspirant base, the remainder being water, inert solvents and/or excipients, and optionally, disinfecting, germicidal or bacteriostatic agents.

3. A perfumed composition according to claim 1, characterised in that the antiperspirant base consists of an aluminium salt.

4. A perfumed composition according to claim 3, characterised in that the aluminium salt is an aluminium chlorohydrate.

5. A deodorant or antiperspirant device or article for use in personal care, characterised in that it contains a perfuming composition according to claim 1.

6. A deodorant or antiperspirant device or article according to claim 5 chosen from creams, sticks, roll-ons, smooth-ons, aerosols or powders.

* * * * *

UNITED STATES PATENT AND TRADEMARK OFFICE
CERTIFICATE OF CORRECTION

PATENT NO. : 4,803,195
DATED : February 7, 1989
INVENTOR(S) : Gunter Holzner

It is certified that error appears in the above-identified patent and that said Letters Patent is hereby corrected as shown below:

Column 3, lines 9-11: should read as follows:

substrate. Due to subsequent drying, which is effected simply by the exposure to air of the skin thus treated and which is assisted by the body heat, the active per- Column 4, line 17:

change "substate" to --substrate--.

Signed and Sealed this

Eighth Day of August, 1989

Attest:

DONALD J. QUIGG

Attesting Officer      Commissioner of Patents and Trademarks